United States Patent [19]

Shinohara

[11] Patent Number: 4,551,138

[45] Date of Patent: Nov. 5, 1985

[54] CANNULA DEVICE AND MEDICAL BAG HAVING THE SAME

[75] Inventor: Shuichi Shinohara, Fuji, Japan

[73] Assignee: Terumo Kabushiki Kaisha, Tokyo, Japan

[21] Appl. No.: 714,342

[22] Filed: Mar. 20, 1985

Related U.S. Application Data

[63] Continuation of Ser. No. 422,942, Sep. 24, 1982, abandoned.

[30] Foreign Application Priority Data

Mar. 12, 1982 [JP]  Japan .................................. 57-39244

[51] Int. Cl.⁴ .............................................. A61M 5/14
[52] U.S. Cl. ..................... 604/262; 604/192; 604/199; 604/263; 604/408
[58] Field of Search ................ 604/192, 193, 197–199, 604/256, 262–264, 280, 283, 905, 411; 206/364–365

[56] References Cited

U.S. PATENT DOCUMENTS

| | | | |
|---|---|---|---|
| 2,400,722 | 5/1946 | Swan | 604/192 |
| 2,539,510 | 1/1951 | Friden | 604/192 |
| 3,545,607 | 12/1970 | Keller | 604/193 |
| 4,007,740 | 2/1977 | Owen | 604/263 |
| 4,085,737 | 4/1978 | Bordow | 604/198 |
| 4,091,811 | 5/1978 | Bates et al. | 604/263 |
| 4,124,025 | 11/1978 | Alrazi | 604/263 |
| 4,317,446 | 3/1982 | Ambrosio et al. | 604/197 |
| 4,402,682 | 9/1983 | Garver, Sr. et al. | 604/283 |

FOREIGN PATENT DOCUMENTS 55-49075  11/1980  Japan .................................. 604/192

Primary Examiner—C. Fred Rosenbaum
Assistant Examiner—Michelle N. Lester
Attorney, Agent, or Firm—Frishauf, Holtz, Goodman & Woodward

[57] ABSTRACT

A cannula device has a hollow needle, and a hub which supports the hollow needle at the proximal end portion thereof and which is made of a hard plastic. A protector comprises a hollow body whose distal end is closed and whose proximal end is open and which is made of a hard plastic. The protector is detachably mounted on the hub such that the hollow body houses the hollow needle therein and the proximal end of the hollow body covers the distal end portion of the hub. A resilient layer is formed between the inner circumferential surface of the proximal end portion of the hollow body and the outer circumferential surface of the distal end portion of the hub.

40 Claims, 6 Drawing Figures

CANNULA DEVICE AND MEDICAL BAG HAVING THE SAME

This application is a continuation, of application Ser. No. 422,942, filed Sept. 24, 1982, abandoned.

BACKGROUND OF THE INVENTION

I. Field of the Invention

The present invention relates to a cannula device used as a medical instrument and to a medical bag provided with such a cannula device.

II. Description of the Prior Art

A needle of a syringe or a cannula which is connected to a fluid therapy bag or a blood transfusion bag, and which is pierced into the body of a patient as needed, generally comprises a hollow needle and a hub supporting the hollow needle at the proximal end portion thereof. The hub of the cannula which is most frequently used at present is made of a hard plastic such as polyvinyl chloride, and a hollow needle is inserted into the hub. In order to securely hold the hollow needle to the hub, a layer of a thermoset resin such as a cured epoxy resin is formed on the distal end plane of the hub to be integral with the outer circumferential surface of the hollow needle.

In order to protect such a cannula from damage due to an external impact until actual use, the cannula as described above is generally capped with a protector which is made of a hard plastic (generally a plastic harder than that of the hub). The protector comprises a hollow body whose one end is open and whose other end is closed. The hollow needle is inserted inside the hollow body. The outer diameter of the distal end portion of the hub is generally greater than the inner diameter of the open end of the protector by about 0.1 to 0.2 mm. Due to this difference, when the protector is placed over the cannula, the distal end portion of the hub is slightly reduced in diameter. Although the open end of the protector is slightly enlarged in diameter, the degree of enlargement is smaller than the degree of reduction in diameter at the distal end portion of the hub. The cannula, capped with the protector, is subjected to autoclaving sterilization.

If the epoxy resin for fixing the hollow needle to the hub is not completely cured in a cannula of the type as described above, the degree of reduction in diameter at the distal end portion of the hub upon being capped with the protector becomes too great. This substantially eliminates the difference in the outer diameter of the hub at the distal end portion thereof and the inner diameter of the protector, resulting in a poor hermetic or liquid-tight seal. This phenomenon is frequently made more pronounced by autoclaving sterilization. If a cannula device in this condition is connected to a bag holding an infusion solution or the like therein, the liquid which happens to be introduced into the protector from the bag through the hollow needle may leak to the outside through a contact portion between the hub and the protector. With such a cannula device, ambient air may also be introduced into the device through the contact portion between the hub and the protector, resulting in poor hygiene.

On the other hand, if the epoxy resin is excessively cured, any reduction in the diameter of the hub is difficult. If the protector is forcibly placed over the distal end portion of the hub, removal thereof is not easy. In addition, when the protector is placed over the device, the inner surface of the protector may be axially scratched due to the presence of too hard an epoxy resin layer. Since the diameter of the hub does hardly decrease, the scratches thus formed impair the hermetic or liquid-tight seal between the hub and the protector and present a similar problem as that encountered when the epoxy resin is not completely cured. This phenomenon is also made more pronounced by the heat of autoclaving sterilization.

SUMMARY OF THE INVENTION

It is an object of the present invention to provide a cannula device comprising a hollow needle supported by a hub and a protector for protecting the hollow needle, wherein the protector smoothly and detachably covers the hub with a hermetic and liquid-tight seal.

A cannula device of the present invention includes a hollow needle, and a hub of a hard plastic which supports the hollow needle at the proximal end portion thereof. The protector comprises a hollow body whose distal end portion is closed and whose proximal end portion is open, and is made of a hard plastic. The hollow needle is housed inside the hollow body of the protector. The proximal or open end portion of the hollow body of the protector is detachably placed over the distal end portion. A resilient layer is formed at an area between the inner circumferential surface of the hollow body and the outer circumferential surface of the hub.

The resilient layer is fixed onto the inner circumferential surface of the hollow body at the proximal end portion thereof or onto the outer circumferential surface of the hub at the distal end portion thereof.

The present invention also provides a medical bag for holding a liquid to which a cannula device as described above is connected through a tube.

DETAILED DESCRIPTION OF THE PREFERRED EMBODIMENTS

Figure 1A:
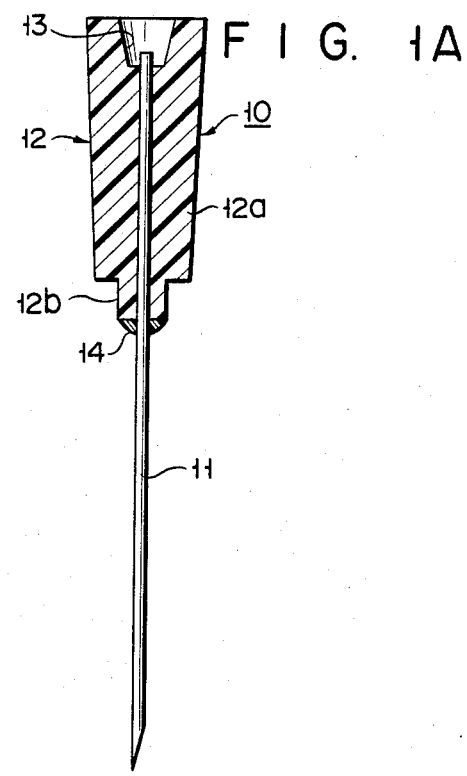
FIGS. 1A and 1B are sectional views respectively showing a cannula and a protector of a cannula device according to a first embodiment of the present invention.

The present invention will now be described in detail with reference to the accompanying drawings. The same reference numerals denote the same parts throughout the drawings.

Figure 1B:
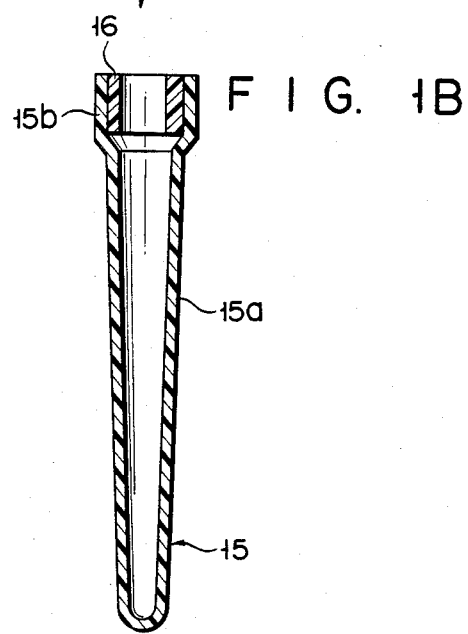
Figure 2:
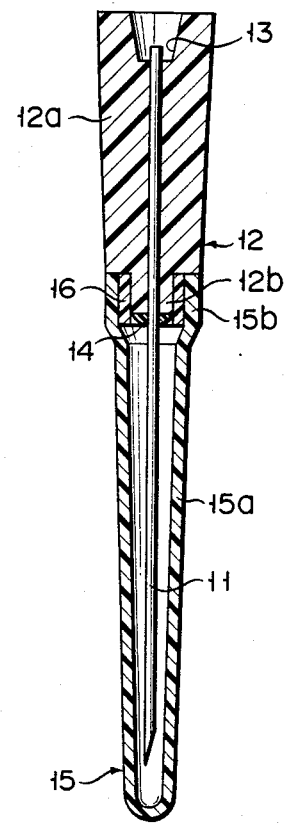
FIG. 2 is a sectional view showing a combined state of the cannula shown in FIG. 1A and the protector shown in FIG. 1B.

FIGS. 1A and 1B and 2 show the first embodiment of the present invention. As shown in FIG. 1A, a cannula 10 of a cannula device of this embodiment has a hollow needle 11 whose distal end portion is pointed, and a hub 12 which supports the hollow needle 11 at the proximal end portion thereof. The hub 12 comprises a main body 12a and a small columnar body 12b. The main body 12a has a frustoconical shape close to a columnar shape wherein the angle of the side surface with respect to the lower end face is close to a right angle. The columnar body 12b has a diameter smaller than the diameter of that upper end face of the main body 12a with which the body 12b is integral and is integrally mounted at the center of the upper end face of the main body 12a. A tapered recess 13 is formed in the lower end face of the main body 12a and is capable of receiving a tube or an outer cylinder of a syringe. The overall hub 12 is made of a hard plastic material, more particularly, of a hard plastic material which has a heat resistance capable of withstanding autoclaving sterilization (generally placement in a saturated steam of 115° to 133° C. for 5 to 30 minutes). Examples of such hard plastic materials include polyurethane, polyvinyl chloride and polycarbonate.

The hollow needle 11 extends along the axis of the hub 12, and its proximal end slightly extends into the recess 13. In order to securely fix the hollow needle 11 to the hub 12, an epoxy-type adhesive 14 is applied to the end face of the columnar body 12b of the hub 12 to surround a portion of the hollow needle 11.

As shown in FIG. 1B, a protector 15 has a hollow main body 15a whose proximal end is open and whose distal end is closed, and a hollow cylindrical body 15b which is formed integrally with the main body 15a and which has an inner diameter slightly larger than that of the main body 15a. The protector 15 is made of a hard plastic material, more particularly, of a material which has a heat resistance capable of withstanding autoclaving sterilization. The protector 15 is preferably made of a transparent material. In this case, whether or not the pointed end of the hollow needle 11 is deformed after the cannular 10 is capped with the protector 15, and whether or not any foreign material is attached to the hollow needle, may be confirmed with an eye without requiring removal of the protector 15. Examples of such a material for the protector 15 include polyvinyl chloride, polycarbonate, polypropylene, polyethylene, polyester and poly(methyl pentene). Since the overall protector 15 is made of a hard plastic material, once it covers the cannula, no external force may act on the protector so as to directly act on the hollow needle and damage it as in the case when the protector is made of a resilient material.

A resilient layer 16 is formed on the inner circumferential surface of the cylindrical body 15b of the protector 15. Although the material of the resilient layer 16 is not particularly limited, it is preferably a polymeric elastomer. Examples of such a polymeric elastomer include cross-linked (including vulcanized) type rubbers such as cross-linked natural rubber, synthetic natural rubber, styrene-butadiene rubber, butadiene rubber, chloroprene rubber, nitrile rubber, butyl rubber, ethylene-propylene rubber, and urethane rubber; synthetic resin elastomers including plastic elastomers such as polyolefin elastomer, polyamide elastomer, polyester elastomer, polyurethane elastomer, a styrene block-type elastomer and silicone rubber. The resilient layer 16 preferably has a hardness of 30 to 80 according to JIS K6301. Because of durability of air- and liquid-tightness and smooth fitting and detaching of the protector into and from the hub, the resilient layer 16 preferably has a compression set of 20 to 80% after heating at 100° C. for 22 hours according to JIS K6301, since it must provide a hermetic and liquid-tight seal between the hub 12 and the protector 15 after autoclaving sterilization. The materials for such a resilient layer 16 may be selected from the polymeric elastomers as described above.

The resilient layer 16 may be manufactured simultaneously as the protector 15 by the two-color molding method wherein two different types of materials are simultaneously or sequentially molded within a single mold. This two-color molding method improves the productivity, and adhesion between the protector 15 and the resilient layer 16 is excellent. The protector 15 and the resilient layer 16 may alternatively be manufactured by insertion molding or the like. The protector 15 and the resilient layer 16 may be separately molded, and then the resilient layer 16 may be joined to the inner circumferential surface of the protector 15.

The cannula 10 and the protector 15 are assembled together such that the cylindrical body 15b of the protector 15 covers the columnar body 12b of the hub 12, as shown in FIG. 2. Thus, the resilient layer 16 is interposed between the cylindrical body 15b of the protector 15 and the columnar body 12b of the hub 12.

The inner diameter of the cylindrical body 15b of the protector 15 is generally less than the outer diameter of the columnar body 12b of the hub 12 by 0.1 to 0.5 mm. The resilient layer 16 generally has a thickness of 0.3 to 2.0 mm. When the protector 15 and the cannula 10 are assembled in the manner as shown in FIG. 2, the resilient layer 16 is compressed. Due to the resultant repelling force and resiliency, the cylindrical body 15b of the protector 15 and the columnar body 12b of the hub 12 are hermetically and liquid-tightly sealed. The resilient layer 16 serves to absorb any external force. Even if the epoxy-type adhesive 14 is not sufficiently cured, when the cylindrical body 15b of the protector 15 is placed over the columnar body 12b of the hub 12 of the cannula 10 during assembly of the cannula 10 and the protector 15, the columnar body 12b may not be reduced in diameter as in the conventional case. Even if the epoxy resin 14 is excessively cured, removal of the cylindrical body 15b is not difficult and the inner surface of the cylindrical body 15b is not damaged, facilitating smooth covering and removal. The protector 15 and the cannula 10 are subjected to autoclaving sterilization in the assembled state as shown in FIG. 2. Even if the cylindrical body 15b of the protector 15 or the columnar body 12b of the hub 12 is thermally deformed slightly due to the heat of sterilization, the resilient layer 16 resiliently absorbs such deformation and may not therefore impair the hermetic and liquid-tight seal. For example, when the distal end portion of an outer cylinder of a syringe holding an infusion solution therein is fitted into the recess 13 of the hub 12, even if the infusion solution leaks into the protector 15 through the hollow needle 11, the infusion solution may not leak to the outside between the columnar body 12b of the hub 12 and the cylindrical body 15b of the protector 15. Even if an external force acts on the assembly of the cannula 10 and the protector 15, the resilient layer 16 serves to absorb any such external force to stably keep the hermetic and liquid-tight seals therebetween.

The resilient layer 16 may be formed over the entire inner surface of the protector 15. In this case, even if the pointed end of the hollow needle 11 contacts the inner surface of the protector 15 when the protector 15 is placed over the cannula 10, the protector 15 may not be damaged due to the presence of the resilient layer 16.

Figure 3A:
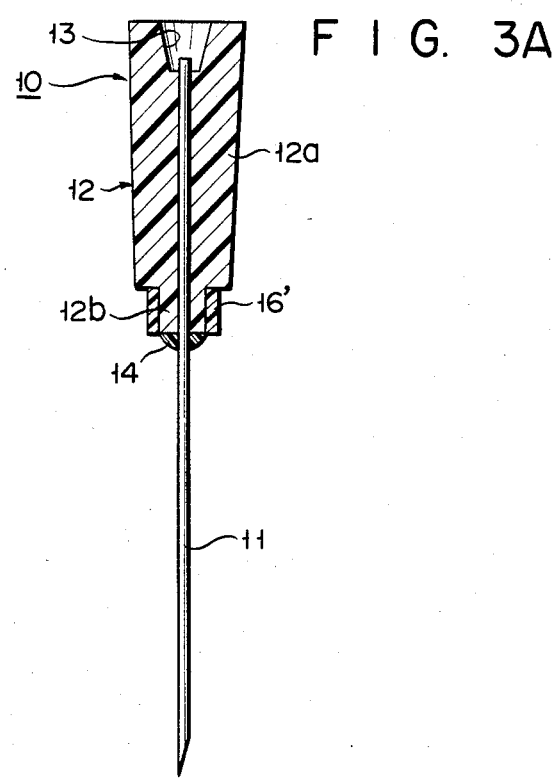
FIGS. 3A and 3B are sectional views respectively showing a cannula and a protector of a cannula device according to a second embodiment of the present invention.
Figure 3B:
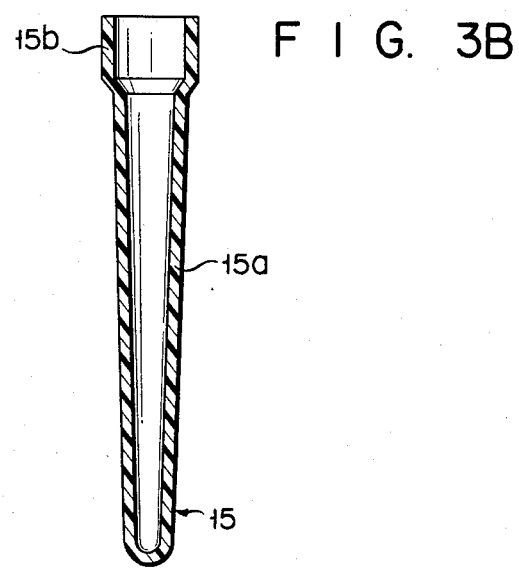

FIGS. 3A and 3B respectively show a cannula and a protector of a cannula device according to the second embodiment of the present invention. The second embodiment is basically the same as the first embodiment shown in FIGS. 1A and 1B except that a resilient layer 16' is formed on the outer circumferential surface of the columnar body 12b of the hub 12. In order to securely adhere the resilient layer 16' to the outer circumferential surface of the columnar body 12b, the similar method to that for forming the resilient layer 16 on the inner circumferential surface of the cylindrical body 15b of the protector 15 of the first embodiment may also be adopted.

Figure 4:
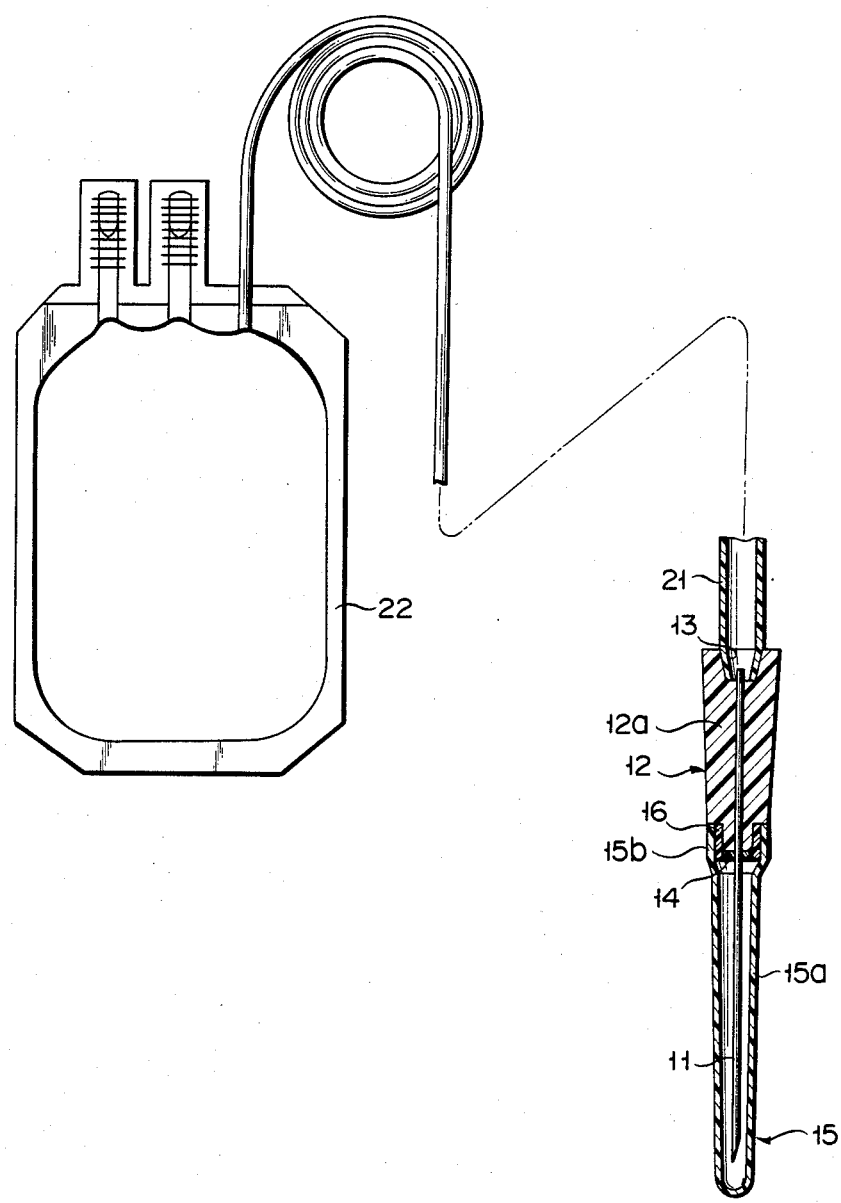
FIG. 4 is a view showing a medical bag having a cannula device according to the present invention.

FIG. 4 shows a medical bag having a cannula device as described above. One end of a tube 21 is fitted into the recess 13 formed in the main body 12a of the cannula capped with the protector 15 as shown in FIG. 2, and the other end of the tube 21 is connected to a bag 22. The bag 22 may be a fluid therapy bag or a blood transfusion bag and holds therein a fluid therapy agent, a blood anticoagulant solution (citric acid, sodium citrate, grape sugar, or sodium phosphate), or the like. The bag 22 is made of a flexible plastic. It is to be noted that the cannula device used in this embodiment may be replaced by the cannula device shown in FIG. 3.

According to this embodiment, the joint surface of the hub 12 of the cannula 10 and the protector 15 is kept liquid-tight due to the presence of the resilient layer 16. Therefore, in both use and non-use states of the cannula 10, the solution held in the bag 22 may not leak through the joint surface. Even if various external forces act on the cannula 10, the joint surface is kept liquid-tight.

Since the bag 22 is made of a flexible plastic, the bag 22 deforms as the solution held therein is discharged. Therefore, the solution may be discharged without introducing ambient air into the bag. Contamination of the bag due to introduction of ambient air is thus prevented. The space for the bag or bags is reduced during storage as compared to the case of glass bottles.

What is claimed is:

1. An autoclave-sterilized cannula device, comprising:
    a hollow needle;
    a hub which supports said hollow needle at a proximal end portion of said hollow needle and which is made of a hard plastic;
    a protector comprising a hollow body whose distal end portion is closed and whose proximal end portion is open and which is made of a hard plastic, said protector being detachably mounted on said hub such that said hollow body houses said hollow needle therein, and said proximal end portion of said hollow body covers a distal end portion of said hub; and
    a resilient layer which is formed between an inner circumferential surface of said proximal end portion of said hollow body and an outer circumferential surface of said distal end portion of said hub, wherein said resilient layer has a hardness in the range of 30 to 80 and a compression set of 20-80% after heating at 100° C. for 22 hours;
    wherein said resilient layer is operative to maintain a hermetic seal between said hub and said protector both before and after being subjected to an autoclave sterilization environment, and wherein said resilient layer is operative to also maintain a liquid-tight seal between said hub and said protector after being subjected to said autoclave sterilization environment.

2. A device according to claim 1, wherein said resilient layer is arranged to provide surface-to-surface contact with said proximal end portion of said hollow body and said outer circumferential surface of said distal end portion of said hub over at least a substantial portion of the length of the end portion of said hollow body which covers said distal end portion of said hub.

3. A device according to claim 1, wherein said resilient layer is made of a polymeric elastomer.

4. A device according to claim 3, wherein said polymeric elastomer is a cross-linked type rubber or a synthetic resin elastomer.

5. A device according to claim 4, wherein said cross-linked type rubber is selected from the group consisting of natural rubber, synthetic natural rubber, styrene-butadiene rubber, butadiene rubber, chloroprene rubber, nitrile rubber, butyl rubber, ethylene-propylene rubber, urethane rubber and silicone rubber.

6. A device according to claim 4, wherein said synthetic resin elastomer is selected from the group consisting of polyolefin elastomer, polyamide elastomer, polyester elastomer, polyurethane elastomer and a styrene block-type elastomer.

7. A device according to claim 1, wherein said protector is made of a heat-resistant material.

8. A device according to claim 7, wherein said protector is transparent.

9. A device according to claim 8, wherein said protector is made of a member selected from the group consisting of polyvinyl chloride, polycarbonate, polypropylene, polyethylene, polyester and poly(methyl pentene).

10. A device according to claim 1, wherein said hub is made of a heat-resistant material.

11. A device according to claim 10, wherein said hub is made of a member selected from the group consisting of polyurethane, polyvinyl chloride, and polycarbonate.

12. A device according to claim 10, wherein said hub has a recess at said proximal end portion thereof.

13. A device according to claim 10, wherein said hub comprises a frustoconical main body, and a columnar body which is formed integrally with an upper end face of said frustoconical main body and which has a diameter smaller than a diameter of the upper end face of said frustoconical main body.

14. A device according to claim 1, wherein said resilient layer is formed on the inner circumferential surface of said proximal end portion of said protector.

15. A device according to claim 14, wherein said resilient layer and said protector constitute a two-color-part.

16. A device according to claim 14, wherein said resilient layer and said protector constitute an insert molding.

17. A device according to claim 1, wherein said resilient layer is formed on the outer circumferential surface of said distal end portion of said hub.

18. A device according to claim 17, wherein said resilient layer and said hub constitute an insert molding.

19. A device according to claim 17, wherein said resilient layer and said hub constitute a two-color-part.

20. An autoclave-sterilized medical bag device, comprising:
    a bag for holding a medical solution therein;
    a hollow needle;
    a hub which supports said hollow needle at a proximal end portion of said hollow needle and which is made of a hard plastic;
    a protector comprising a hollow body whose distal end portion is closed and whose proximal end portion is open at which is made of a hard plastic, said protector being detachably mounted on said hub such that said hollow body houses said hollow needle therein, and said proximal end portion of said hollow body covers a distal end portion of said hub;

a resilient layer which is formed between an inner circumferential surface of said proximal end portion of said hollow body and an outer circumferential surface of said distal end portion of said hub, wherein said resilient layer has a hardness of 30–80 and a compression set of 20 to 80% after heating at 100° C. for 22 hours; and a tube whose one end is connected to said proximal end portion of said hub to communicate with said hollow needle, and whose other end is connected to said bag;

wherein said resilient layer is operative to maintain a hermetic seal between said hub and said protector both before and after being subjected to an autoclave sterilization environment, and wherein said resilient layer is operative to also maintain a liquid-tight seal between said hub and said protector after being subjected to said autoclave sterilization environment.

21. A device according to claim 20, wherein said resilient layer is arranged to provide surface-to-surface contact with said proximal end portion of said hollow body and said outer circumferential surface of said distal end portion of said hub over at least a substantial portion of the length of the end portion of said hollow body which covers said distal end portion of said hub.

22. A device according to claim 21, wherein said bag is made of a flexible plastic.

23. A device according to claim 22, wherein said bag is arranged to hold a blood anticoagulant solution.

24. A device according to claim 21, wherein said resilient layer is made of a polymeric elastomer.

25. A device according to claim 24, wherein said polymeric elastomer is a cross-linked type rubber or a synthetic resin elastomer.

26. A device according to claim 25, wherein said cross-linked type rubber is selected from the group consisting of natural rubber, synthetic natural rubber, styrene-butadiene rubber, butadiene rubber, chloroprene rubber, nitrile rubber, butyl rubber, ethylene-propylene rubber, urethane rubber and silicone rubber.

27. A device according to claim 25, wherein said synthetic resin elastomer is selected from the group consisting of polyolefin elastomer, polyamide elastomer, polyester elastomer, polyurethane elastomer and a styrene block-type elastomer.

28. A device according to claim 20, wherein said protector is made of a heat-resistant material.

29. A device according to claim 28, wherein said protector is transparent.

30. A device according to claim 29, wherein said protector is made of a member selected from the group consisting of polyvinyl chloride, polycarbonate, polypropylene, polyethylene, polyester and poly(methyl pentene).

31. A device according to claim 20, wherein said hub is made of a heat-resistant material.

32. A device according to claim 31, wherein said hub is made of a member selected from the group consisting of polyurethane, polyvinyl chloride, and polycarbonate.

33. A device according to claim 31, wherein said hub has a recess at said proximal end portion thereof.

34. A device according to claim 31, wherein said hub comprises a frustoconical main body, and a columnar body which is formed integrally with an upper end face of said frustoconical main body and which has a diameter smaller than a diameter of the upper end face of said frustoconical main body.

35. A device according to claim 20, wherein said resilient layer is formed on the inner circumferential surface of said proximal end portion of said protector.

36. A device according to claim 35, wherein said resilient layer and said protector constitute a two-color-part.

37. A device according to claim 35, wherein said resilient layer and said protector constitute an insert molding.

38. A device according to claim 20, wherein said resilient layer is formed on the outer circumferential surface of said distal end portion of said hub.

39. A device according to claim 38, wherein said resilient layer and said hub constitute an insert molding.

40. A device according to claim 38, wherein said resilient layer and said hub constitute a two-color-part.

* * * * *